United States Patent
Byrom et al.

(10) Patent No.: US 11,170,875 B2
(45) Date of Patent: Nov. 9, 2021

(54) METHODS AND APPARATUS FOR DATA-DRIVEN MONITORING

(71) Applicant: PAREXEL International Corporation, Waltham, MA (US)

(72) Inventors: William Byrom, West Bridgford (GB); Elizabeth H. Love, Badsey (GB); Petra Stachon, Berlin (DE); Casey McInnis, Billerica, MA (US); Christie G. Wilkins, Billerica, MA (US); Drew J. Garty, Billerica, MA (US); Matthew Flynn, Billerica, MA (US); Joanne White, Billerica, MA (US); Catalina Sarbu, Bucharest (RO); Nancy Winter, Nottingham (GB)

(73) Assignee: PI Blocker Corporation, Morrisville, NC (US)

( * ) Notice: Subject to any disclaimer, the term of this patent is extended or adjusted under 35 U.S.C. 154(b) by 78 days.

(21) Appl. No.: 14/175,469

(22) Filed: Feb. 7, 2014

(65) Prior Publication Data

US 2014/0249835 A1  Sep. 4, 2014

Related U.S. Application Data

(60) Provisional application No. 61/762,509, filed on Feb. 8, 2013.

(51) Int. Cl.
*G16H 10/60* (2018.01)
*G16H 10/20* (2018.01)

(52) U.S. Cl.
CPC ................ *G16H 10/20* (2018.01)

(58) Field of Classification Search
CPC .. G06Q 50/24; G06Q 10/0635; G06F 19/363; G16H 10/20; G16H 10/60
USPC .......................................................... 705/2
See application file for complete search history.

(56) References Cited

U.S. PATENT DOCUMENTS

| | | | |
|---|---|---|---|
| 5,666,490 A | 9/1997 | Gillings et al. | |
| 7,054,823 B1 | 5/2006 | Briegs et al. | |
| 8,620,680 B2 | 12/2013 | Schultz | |
| 8,706,537 B1 * | 4/2014 | Young | G06Q 10/10 705/7.11 |

(Continued)

FOREIGN PATENT DOCUMENTS

WO   WO-2013173715 A1 * 11/2013  ............ G16H 40/20

OTHER PUBLICATIONS

Neela D. Goswami, The State of Infectious Diseases Clinical Trials: A Systematic Review of ClinicalTrials.gov, Oct. 2013 https://ip.com/npl/pmc/PMC3797691 PMC3797691 (Year: 2013).*

(Continued)

*Primary Examiner* — Hiep V Nguyen
(74) *Attorney, Agent, or Firm* — Wolf, Greenfield & Sacks, P.C.

(57) ABSTRACT

Methods and apparatus for facilitating monitoring in a clinical trial. The method includes acts of receiving data from at least one information technology system configured to process clinical trial data, and assigning a site prioritization to each of a plurality of sites for at least one clinical trial associated with the at least one information technology system. Assigning a site prioritization is based, at least in part, on the received data. The method further includes an act of outputting an indication of the site prioritization.

36 Claims, 8 Drawing Sheets

(56) References Cited

U.S. PATENT DOCUMENTS

| | | | |
|---|---|---|---|
| 9,092,566 | B2 | 7/2015 | Buyse et al. |
| 10,311,534 | B2 | 6/2019 | Schultz |
| 2003/0065669 | A1 | 4/2003 | Kahn et al. |
| 2003/0097291 | A1 | 5/2003 | Freedman |
| 2004/0078216 | A1 | 4/2004 | Toto |
| 2004/0249664 | A1 | 12/2004 | Broverman et al. |
| 2005/0182657 | A1 | 8/2005 | Abraham-Fuchs |
| 2005/0182663 | A1* | 8/2005 | Abraham-Fuchs .... G06Q 50/24 705/3 |
| 2005/0182664 | A1 | 8/2005 | Abraham-Fuchs et al. |
| 2006/0143047 | A1 | 12/2006 | Briegs et al. |
| 2006/0282244 | A1 | 12/2006 | Chotai et al. |
| 2007/0067189 | A1 | 3/2007 | Boris et al. |
| 2008/0270181 | A1 | 10/2008 | Rosenberg |
| 2009/0292554 | A1 | 11/2009 | Schultz |
| 2010/0114594 | A1 | 5/2010 | Schultz |
| 2010/0169114 | A1* | 7/2010 | Henderson ............. G06Q 10/00 705/2 |
| 2013/0311196 | A1* | 11/2013 | Fay .................... G06Q 10/0635 705/2 |
| 2014/0324553 | A1* | 10/2014 | Rosenberg ....... G06Q 10/06395 705/7.41 |
| 2019/0287198 | A1 | 9/2019 | Schultz |

OTHER PUBLICATIONS

U.S. Appl. No. 12/431,612, filed Apr. 28, 2009, Joshua Schultz.

International Search Report and Written Opinion for PCT/US2014/015224, dated Jul. 23, 2014.

European Patent Office, Notice from the European Patent Office dated Oct. 1, 2007 concerning business methods. Official Journal of the European Patent Office Nov. 1, 2007; 592-593.

European Patent Office, Statement in accordance with the Notice from the European Patent Office dated Oct. 1, 2007 concerning business methods (OJ EPO dated Nov. 2007, 592-593) dated Nov. 1, 2007.

EClinical Forum Risk Based Monitoring Taskforce, "Risk-Based Approaches", 22 pgs., Sep. 15, 2012.

Guidance for Industry Oversight of Clinical Investigations—A Risk-Based Approach to Monitoring, Aug. 24, 2011, 18 pages.

Risk-adapted Approaches to the Management of Clinical Trials of Investigational Medicinal Products, MRC/DH/MHRA Joint Project, Oct. 10, 2011, 31 pages.

Position Paper: Risk-Based Monitoring Methodology, TransCelerate BioPharma Inc., May 30, 2013, 33 pages.

International Preliminary Report on Patentability dated Aug. 20, 2015 for Application No. PCT/US2014/015224.

\* cited by examiner

METHODS AND APPARATUS FOR DATA-DRIVEN MONITORING

RELATED APPLICATIONS

This application claims the benefit of U.S. Provisional Application Ser. No. 61/762,509 filed on Feb. 8, 2013, the contents of which are incorporated by reference herein.

BACKGROUND

Obtaining approval for an investigational product (e.g., a medical device, a pharmaceutical product such as a drug, etc.) requires a clinical trial in which the investigational product is tested on human subjects to demonstrate the product's safety and efficacy for its intended purpose. To ensure that the results of the clinical trials are reliable and that results are reproducible, many clinical trials are often multi-site and/or multinational operations which typically require substantial planning and oversight to run efficiently. For example, a clinical trial may involve hundreds or thousands of patients recruited worldwide, and a central management service may be employed to manage various aspects of the clinical trial.

One aspect of clinical trials that central management services are often employed to manage relates to providing and/or coordinating monitoring resources (e.g., scheduling site-monitoring visits) to particular sites involved in the clinical trial. During a site visit, clinical trial monitors (also referred to herein as "clinical research associates" or "CRAs") are asked to perform a variety of tasks such as, verifying that data has been entered correctly by site personnel, investigating any reported adverse events, following up on site issues or protocol deviations, and checking that the investigational product is properly labeled, stored, and inventoried at the site.

SUMMARY

The inventors have recognized and appreciated that conventional techniques for monitoring in a clinical trial may be improved using one or more data-driven processes (also referred to herein as "data-driven monitoring"). To this end, some embodiments are directed to using data stored by systems configured to process clinical trial data to facilitate a coordination of monitoring processes. Data from one or more information technology systems may be used to assign a value to sites, and the value may be used, at least in part, to determine monitoring information for one or more clinical trials. The value assigned to a site may also be determined based, at least in part, on criteria specified by a clinical trial sponsor and/or as indicated in a protocol for a clinical trial. By enabling criteria to be specified for each clinical trial and/or sponsor, the techniques described herein may be configurable to conform to the requirements of individual sponsors and/or protocols and also be flexible to be able to respond to future changes in governmental regulations or guidance regarding the conduct of monitoring for clinical trials.

Some embodiments are directed to a method of facilitating monitoring in a clinical trial. The method comprises receiving data from at least one information technology system configured to process clinical trial data; assigning, using at least one processor, a site prioritization to each of a plurality of sites for at least one clinical trial associated with the at least one information technology system, wherein the assigning a site prioritization is based, at least in part, on the received data; and outputting an indication of the site prioritization.

Other embodiments are directed to a non-transitory computer-readable medium encoded with a plurality of computer-executable instructions that, when executed by at least one processor, performs a method. The method comprises receiving data from at least one information technology system configured to process clinical trial data; assigning a site prioritization to each of a plurality of sites for at least one clinical trial associated with the at least one information technology system, wherein the assigning a site prioritization is based, at least in part, on the received data; and outputting an indication of the site prioritization.

Other embodiments are directed to a computer system. The computer system comprises an input interface configured to receive data from at least one information technology system configured to process clinical trial data and at least one processor. The at least one processor is programmed to assign a site prioritization to each of a plurality of sites for at least one clinical trial associated with the at least one information technology system, wherein the assigning a site prioritization is based, at least in part, on the received data. The computer system further comprises an output device configured to output an indication of the site prioritization.

Other embodiments are directed to predicting a future workload at one or more of a plurality of clinical trial sites, wherein the future workload is determined based, at least in part, on predictive analytics determined based, at least in part, on data received from at least one information technology system, and assigning a site prioritization is based, at least in part, on the predicted future workload at the one or more of the plurality of clinical trial sites.

Other embodiments are directed to receiving criteria including at least one risk indicator, determining a risk score for each of a plurality of clinical trial sites based, at least in part, on data received from at least one information technology system associated with the at least one risk indictor, and assigning the site prioritization for each of the plurality of sites based, at least in part, on a corresponding risk score determined for the site.

Other embodiments are directed to outputting, via a user interface, an indication of the risk score determined for one or more of a plurality of clinical trial sites.

Other embodiments are directed to outputting an indication of a site prioritization in association with monitor scheduling information for the at least one clinical trial, accessing a monitor scheduling system to determine a scheduled monitoring visit for at least one site of a plurality of sites, determining that a risk score for the at least one site is below a threshold value, and outputting an indication that the scheduled monitoring visit for the at least one site should be rescheduled after determining that the risk score for the at least one site is below the threshold value.

Other embodiments are directed to receiving updated data from one or more information technology systems, reassigning based, at least in part, on the updated data, a site prioritization for at least one site of the plurality of sites, and outputting an indication of the reassigned site prioritization.

Other embodiments are directed to generating a monitor scheduling report based, at least in part, on a site prioritization for a clinical trial site.

Other embodiments are directed to generating a monitor scheduling report based, at least in part, on the site prioritization including accessing a monitor scheduling system to determine a scheduled monitoring visit for at least one site of the plurality of sites, determining that the site prioritization for the at least one site is below a threshold value, and outputting an indication that the scheduled monitoring visit for the at least one site should be rescheduled after determining that the site prioritization for the at least one site is below the threshold value, wherein the generated monitor scheduling report includes the indication that the scheduled monitoring visit for the at least one site should be rescheduled.

Other embodiments are directed to outputting an indication of a site prioritization by providing information to a computing system programmed to implement a portion of a clinical trial, wherein the information instructs the computing system to associate one or more of a plurality of sites with a reduced source data verification configuration.

Other embodiments are directed to estimating, based on a site prioritization assigned to at least one of a plurality of sites, a current and/or future monitoring resource requirement.

Other embodiments are directed to estimating a current and/or future resource requirement by estimating a pooled resource requirement for a plurality of studies.

It should be appreciated that all combinations of the foregoing concepts and additional concepts discussed in greater detail below (provided that such concepts are not mutually inconsistent) are contemplated as being part of the inventive subject matter disclosed herein.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
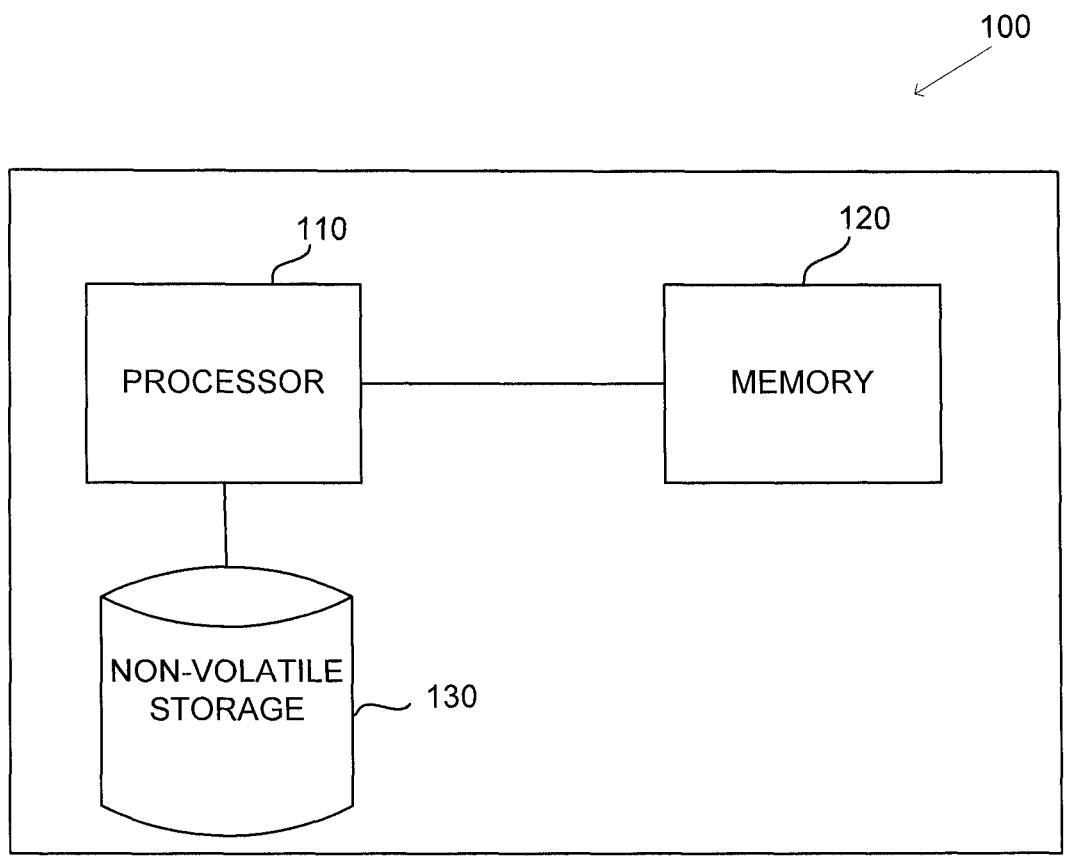
FIG. 1 is an illustrative computer system on which some embodiments of the invention may be implemented.

As discussed above, some conventional techniques for determining a timing and/or frequency of monitoring activities (e.g., scheduling monitoring visits) in clinical trials are often not informed by data-driven processes. Rather, the scheduling of such activities is often driven based on information in a clinical trial protocol that specifies, for example, that monitoring visits to a clinical trial site should occur at periodic intervals (e.g., every 8 weeks). The inventors have recognized and appreciated that, although a clinical trial protocol may set minimum requirements for monitoring in a clinical trial, not all sites in the clinical trial may have the same needs and/or be associated with the same level of risk. To this end, some embodiments of the invention are directed to one or more configurable data-driven processes that output one or more "monitoring values" that provide metrics to enable a user to assess when to perform monitoring activities for specific sites in a clinical trial. For example, output from a data-driven process may be used to decide whether to defer scheduled monitoring visits, reduce a monitoring frequency at specific sites, and/or modify one or more other required activities of a monitor during a site visit to specific sites. The monitoring values, for example, may assign priorities to sites reflecting the priority of that site when assigning monitoring resources.

In accordance with some embodiments, one or more information technology systems configured to process clinical trial data provide data to at least one processor to facilitate monitoring in a clinical trial. The at least one processor may be incorporated as a portion of at least one of the one or more information technology systems or the at least one processor may be connected to the one or more information technology systems via at least one network, as discussed in more detail below.

In some embodiments, data from one or more of the information technology systems may be used to determine various information related to clinical trial monitoring including, but not limited to, a site prioritization, task scheduling and assignment, demonstration of oversight for regulatory compliance, and demonstration of fulfillment of contractual obligations. Some or all of this information may be used to facilitate monitoring decisions as described herein.

The one or more information technology systems may be located in any suitable places and connected in any suitable way using any suitable networks, as embodiments of the invention are not limited in this respect. For example, in some embodiments, one or more information technology systems may be located at a medical services provider 245, while others are located in other places, such as other health care facilities (e.g., hospitals, clinics) or offices of a clinical research organization. Here, medical services provider 245 is shown to contain a medical imaging system. However, it should be appreciated that the specific types of systems present are illustrative and not limiting.

Figure 2:
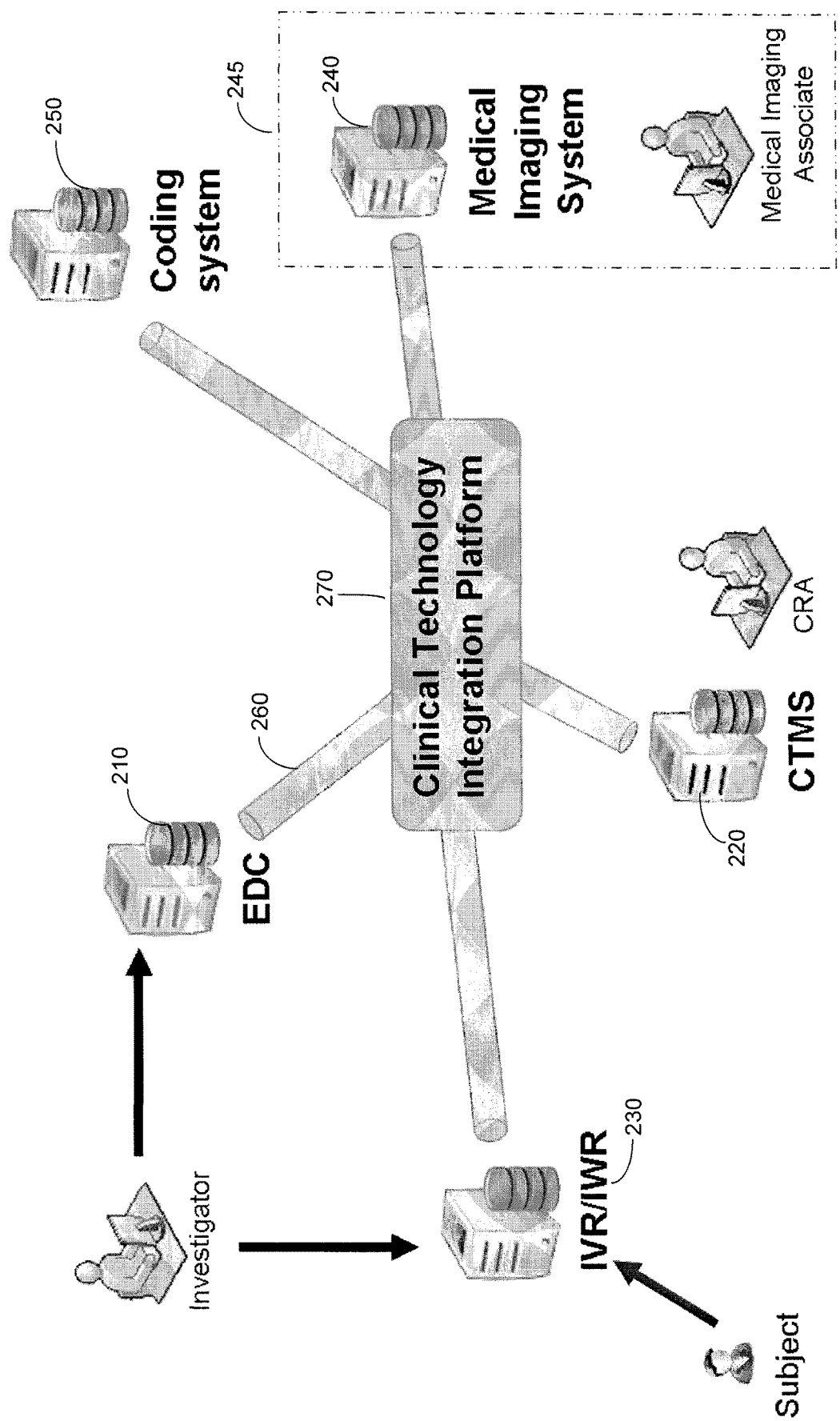
FIG. 2 is an illustrative computer system environment within which some embodiments of the invention may be used.

Regardless of the specific types of systems present, the systems may be connected in any suitable way. For, example, the one or more information technology systems may be connected using a middleware clinical technology integration platform 270 as illustrated in FIG. 2. FIG. 2 illustrates five different information technology systems configured to process clinical trial data (also called "clinical trial systems" herein); electronic data capture (EDC) system 210, clinical trial management system (CTMS) 220, interactive voice response/interactive web response (IVR/IWR) system 230, medical imaging system 240, and coding system 250, each of which is connected via a single connector 260 to a common middleware platform 270, which is a hub through which the integration between systems takes place. Each connector 260 is configured to handle both incoming and outgoing data and transactions to the corresponding system. For example, when a site coordinator enters a new patient visit using one system, an integration message may be automatically sent to other systems. For example, if a new patient visit is entered using EDC 210, an integration message may be sent to IVR/IWR 230 and/or CTMS 220 directly or indirectly via middleware 270. Regardless of where an event, such as entering a new patient visit occurs, the integration message may be translated into information that may be automatically sent to one or more other systems to update data associated with the other systems. In the example above, after receiving a message from EDC 210 that a new patient visit has occurred, middleware 270 may automatically send a message to CTMS 220 to inform the CTMS system that a new patient has occurred and that new data are ready for source data verification (SDV) at the site which entered the new patient visit via EDC 210. SDV, as used herein, describes an amount and/or type of data entered at a clinical trial site to be verified for correctness by a clinical trial monitor. However, it is not a requirement that messages be communicated through middleware, as messages may be communicated in any suitable way.

In the illustrated embodiment, messages may be communicated using software, hardware, or any combination thereof, and embodiments of the invention are not limited in this respect. In a middleware model such as that illustrated in FIG. 2, middleware 270 facilitates the communication of data between connected clinical trial systems by determining which connected clinical trial systems may be updated based on received incoming data and transforming aspects of the incoming data into a format that is expected by destination systems determined by middleware 270 based on the type of incoming data. In other embodiments, destination systems may be determined in any suitable way. Messages including data and/or commands may be sent between connected systems in response to a user's interaction with one or more user interfaces associated with one of the connected systems or messages may be transmitted based on scheduled timepoints (e.g., at a defined time each day. Any suitable action may be performed by middleware 270 or other component upon receiving incoming data, and embodiments of the invention are not limited in this respect. For example, middleware 270 may receive a message from IVR/IWR 230 that a certain quantity of investigational product has been dispensed to patients at a particular site over the past week. This information may be conveyed to CTMS 220 to alert a clinical monitor for the particular site and/or a clinical logistics manager for the clinical trial of an up-to-date status of medication dispensed and remaining at the study site. By communicating this information to CTMS 220, the clinical monitor or clinical logistics manager does not have to search through a report output from an RTSM system to determine that more/less medication should be distributed to sites. Rather, by keeping the information in the CTMS current, the clinical monitor or clinical logistics manager may quickly identify where potential bottlenecks in the clinical trial may occur before such bottlenecks slow down the progress of the clinical trial.

Communication components that route messages between systems may also include one or more security management modules configured to provide appropriate security measures when data is transferred between connected systems and applications. For example, incoming data from a medical services provider 245 may be coded with identifying information for the patient, although it is not necessary that this information be included in the EDC system. Additionally, some connected systems or applications may require that data be encrypted or transferred according to a certain security protocol. The security management module(s) may be configured to ensure that these security requirements are satisfied when transferring data between different clinical trial systems.

In some embodiments, communication components may also include an identity management system that controls users' access to the functionality employed by connected clinical trial systems. Different people involved in a clinical trial may be given different responsibilities, and access to functionality and data in the integrated clinical trial workflow system may be restricted based, at least in part on the user's role in the clinical trial. Furthermore, some users may participate in multiple clinical trials simultaneously, and the access rights for the user may differ for each of the clinical trials in which they are participating. In some embodiments, the identity management system may include an identity management module that is configurable by a system designer to define a level of access for a user based on their defined role in the clinical trial. For example, trial managers may be given a broader scope of access to functionality within the integrated system than clinical trial monitors or other team members. A level of access control that is provided to a user for a particular clinical trial may determine, at least in part, the content displayed on a user interface for the integrated clinical trial workflow system. If the same user is participating in multiple clinical trials, the user interface may be dynamically configured based on the clinical trial that is selected by the user and/or other factors such as the current stage of the clinical trial. For example, in some embodiments relevant monitoring data across multiple clinical trials on which, for example, a trial monitor is assigned may be displayed on the user interface to enable the trial monitor to prioritize tasks across sites and studies. By configuring the user interface in this way, it may be easier for the user to focus on what tasks need to be completed including, but not limited to, responding to queries from other clinical trial personnel, thereby providing an improved workflow for the user.

A middleware model such as that illustrated in FIG. 2 is scalable and flexible because systems and their associated functionality may be added or removed from the system merely by forming or removing a new connector 260 between the system and middleware 270. However, other communications systems may similarly be scalable. Accordingly, virtually any clinical trial system can be integrated in a similar manner as long as it can adhere to the integration standards the connector 260 requires. This type of extensible system provides a simple and repeatable way to enable additional clinical trial systems to be added to the basic building block systems of CTMS, EDC, and RTSM, that are often used in most clinical trials. For example, although not shown in FIG. 2, additional clinical trial systems may include, but are not limited to, ECG management systems, electronic patient reported outcomes systems, drug safety systems, and central laboratory data systems.

In embodiments that use a middleware model such as that illustrated in FIG. 2, middleware 270 may be configured to retrieve data from one or more of the associated information technology systems for use with the techniques described herein to facilitate monitor scheduling. In other embodiments that use point-to-point communications between one or more information technology systems, rather than an integrated platform, one or more processors configured to facilitate monitor scheduling may be designated to retrieve data from the one or more information technology systems. Any suitable number and type of information technology systems configured to process clinical trial data may be used in accordance with the techniques described herein, as the middleware clinical technology integration platform described above, and illustrated in FIG. 2, is merely one example of a type of system environment within which some embodiments of the invention may be used.

Monitoring decisions in a clinical trial may depend, at least in part, on plurality of factors including, but not limited to, an amount of work at a site, a risk assessment of a site, a geographic location of a site, an amount of time that has passed since the last site visit, triggering factors such as adverse events, site issues, reported protocol deviations, interim analysis, emergency code break, or milestones at which source data verification strategies could be adjusted, and clinical trial monitor experience with specific sites. Though, it should be appreciated that factors outside of those collected during a clinical trial may be used as triggering factors, including past performance of a site or regulatory inspection results. In this way, for example, a site with what otherwise might be regarded as a "poor" history may be utilized to perform a clinical trial, but may be assigned to a relatively high risk category.

Figure 3:
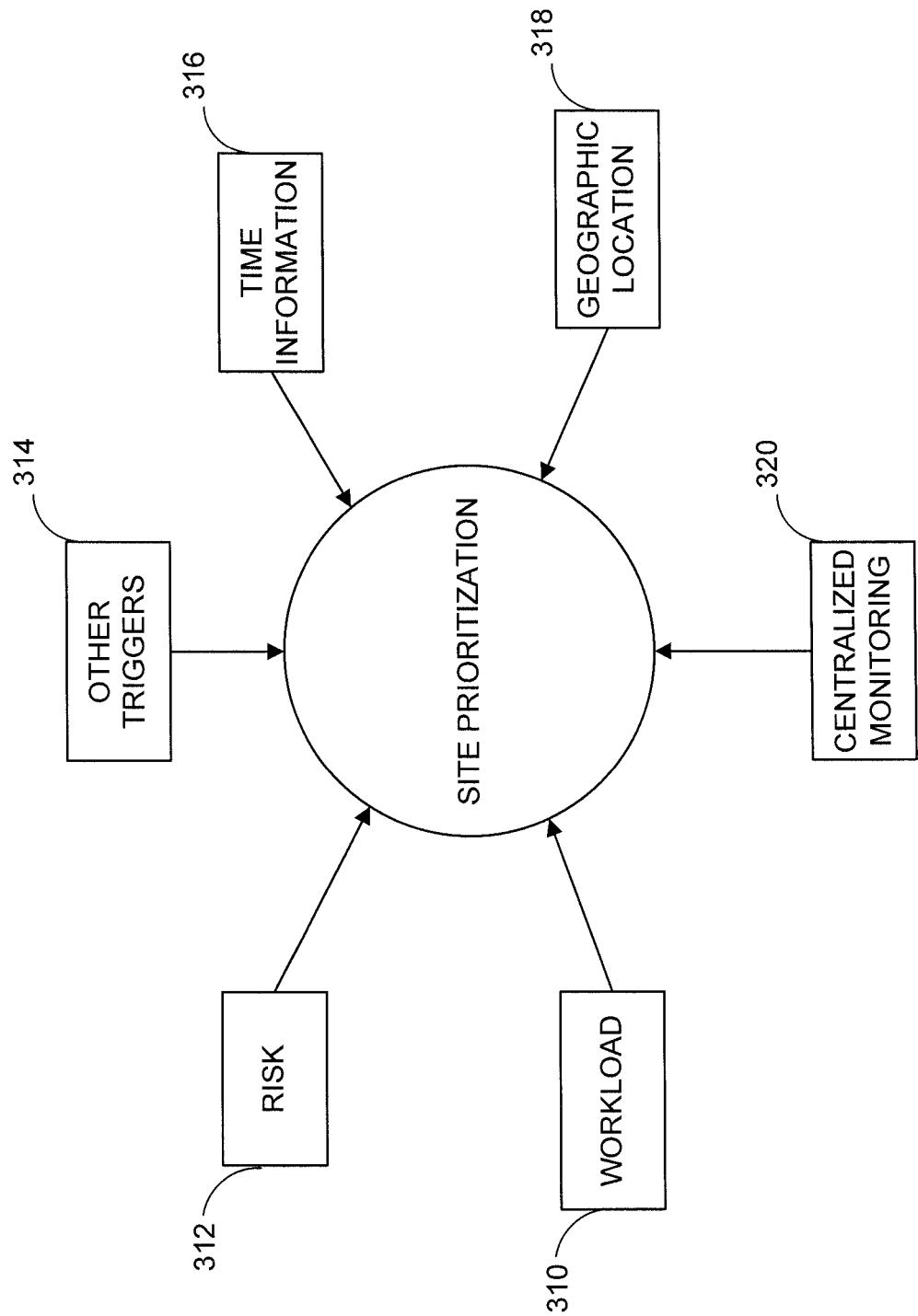
FIG. 3 is a schematic of a plurality of input factors that may be used to determine a site prioritization in accordance with some embodiments of the invention.

FIG. 3 shows a schematic of a plurality of factors that may be used, in accordance with the techniques described herein, to facilitate monitoring for clinical trials. The term "site prioritization" is used herein to refer to a value or values assigned to a site indicating an urgency with which monitoring resources should be assigned to the site. Assigning monitoring resources may include, but is not limited to, initiating "in house" site management activities to address reported issues and/or to reduce risk at the site, performing remote monitoring services, and scheduling a monitoring visit. In some embodiments, a phased approach to assigning monitoring resources may be used to limit a number of on-site monitoring visits. In such a phased approach, site management activities and/or remote monitoring may be applied first prior to scheduling a monitoring visit, though any combination or order of assigning monitoring resources may alternatively be used. For example, in a phased approach, a first intervention may include placing a phone call and/or sending an email to a site to address a reported issue and/or anticipated risk. If that approach does not work satisfactorily to address the concern, a second intervention (e.g., a monitoring site visit) may be assigned to further address the concern.

It should be appreciated that the use of the term "site prioritization" does not necessarily imply a relative measure or any particular ranking of the sites in one or more clinical trials, as in some embodiments, a site prioritization for a particular site may be determined based solely on data associated with that particular site. In other embodiments, a site prioritization for a particular site may be based, at least in part, on data associated with one or more other sites in a clinical trial, as the techniques described herein are not limited in this respect.

As shown in FIG. 3, a site prioritization may be based, at least in part, on workload 310 determined for a particular site. An amount of work at a particular site may be determined in any suitable way. For example, workload may be determined based, at least in part, on outstanding activities (e.g., number of completed case report forms (CRFs), expected investigational product inventory) or any other factors. To determine workload for a particular site, data from one or more information technology systems may be retrieved, and the data may be processed to determine a corresponding workload for the site. For example, a number and/or type of completed CRFs may be retrieved from an EDC system and/or an expected investigational product inventory may be retrieved from an IVR/IWR system, and this data may be used alone, or in combination with other information, to determine a workload for the site.

Figure 4:
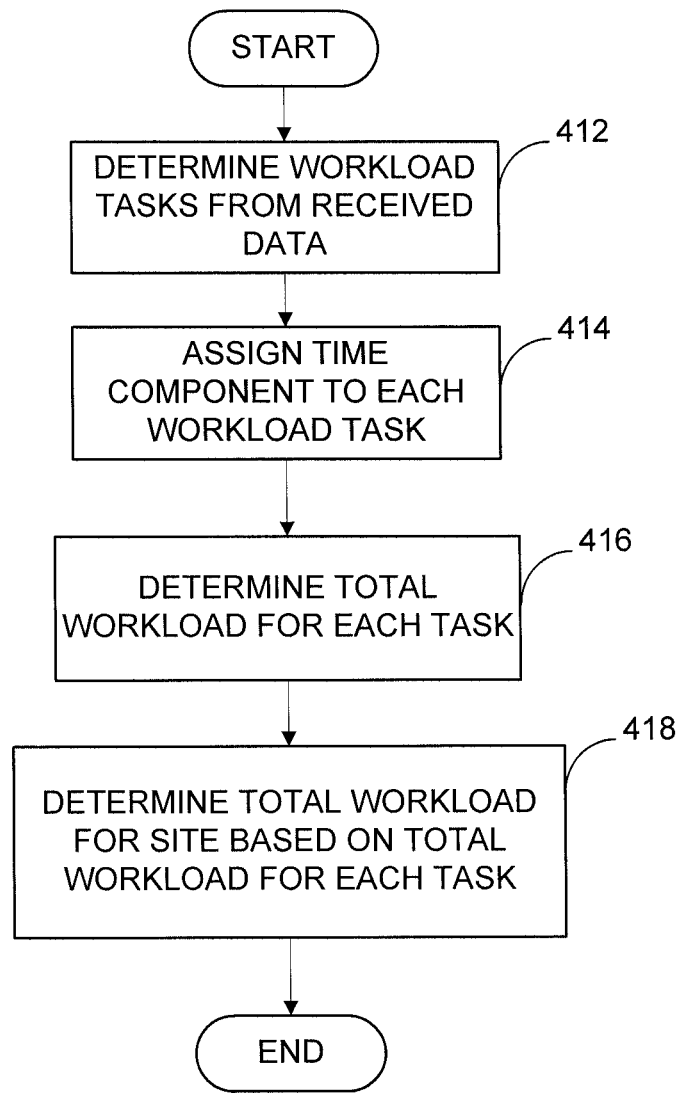
FIG. 4 is a flowchart of an illustrative process for determining a workload for a site in a clinical trial in accordance with some embodiments of the invention.

FIG. 4 shows an illustrative process for determining a workload for a site in accordance with some embodiments of the invention. In act 412, one or more workload tasks are determined from data received from the one or more information technology systems. For example, data received from an EDC system may be used to determine a workload task such as performing source data verification against CRF entries, data received from an RTSM may be used to determine a workload task such as inventorying dispensed and remaining investigational product at a site, and data received from a CTMS system may be used to determine a workload task such as an investigation of protocol deviations. In some embodiments, workload tasks to be determined from data received from the information technology systems may be defined by an authorized user of a clinical trial sponsor or another authorized user. Alternatively, the workload tasks for a clinical trial may be defined in any suitable way, as embodiments of the invention are not limited in this respect.

After the workload tasks have been determined from the received data, the process proceeds to act 414, where a time component is assigned to each of the workload tasks. In some embodiments, the component may be an expected amount of time required to perform a particular workload task. For example, it may be determined that, on average, it takes a monitor two minutes to source verify each CRF page, it takes a monitor one minute to inventory each medication pack or vial, and it takes a monitor twenty minutes to investigate a protocol deviation. Each of these time components may be assigned to its corresponding workload task in any suitable manner. In some embodiments, the time components may be determined by a user associated with a clinical trial sponsor, or the time components may be determined in any other suitable way. In some embodiments, one or more of the time components may be based, at least in part, on historical information indicating a quality assessment of site performance for a particular site in a clinical trial. In some embodiments, the time components assigned to different workload tasks may be updated periodically throughout the course of a clinical trial based, at least in part, on clinical trial monitor experience during the clinical trial. In some embodiments, one or more of the time components associated with workload tasks may be specific to a particular clinical trial monitor assigned to a clinical trial site.

After assigning a time component to each of the workload tasks, the process proceeds to act 416, where a total workload time for each workload task is determined. Continuing with the example above, if the workload task relates to performing source data verification, and the time component associated with this workload task is two minutes, the total workload time for this workload task for a particular site may be calculated as the number of CRF pages to be source verified (e.g., as determined based on received data from an EDC system) multiplied by the assigned time component (e.g., two minutes). Accordingly, if there are 200 CRF pages to source verify at a site, the total time may be 200 pages times two minutes=400 minutes or six hours and forty minutes. Similar calculations may be performed for each of the workload tasks determined in act 412 using the time components assigned in act 414.

After the total workload time has been determined for each of the workload tasks, the process proceeds to act 418, where a total workload for the site is determined based, at least in part, on the total workload determined for each of the plurality of workload tasks. The total workload for a site may be determined in any suitable way, as embodiments of the invention are not limited in this respect. In some embodiments, the total workload for a site may be determined by adding the total workloads determined for each workload task. In other embodiments, one or more of the total workloads determined for the workload tasks may be weighted, such that different workload tasks are emphasized (or de-emphasized) in the determination of the total workload for a site. It should be appreciated that the illustrative process of FIG. 4 does not limit embodiments of the invention, but is provided merely for illustrative purposes, and workload for a site in accordance with the techniques described herein may be determined in any suitable way.

The inventors have recognized and appreciated that some sites in a clinical trial that are associated with less risk, may be good candidates for reduced source data verification (SDV), where the correctness of less than all of the data entered by site personnel must be verified by a clinical trial monitor during a site visit. By not having to verify all of the source data entered by site personnel, the amount of time needed for a site visit may be reduced, resulting in an increased site visit efficiency. Accordingly, in some embodiments, one or more sites in a clinical trial may be specified as a reduced-SDV site. In some embodiments, a reduced-SDV site may be treated differently than other sites. For example, a reduced-SDV site may receive fewer or less frequent monitoring visits. These differences may be implemented in any suitable way, including programming in a clinical trial system that automatically adjusts messages that trigger actions associated with a site. As a more specific example, an EDC system may be programmed to automatically adjust an SDV schedule based on a status of a site as a reduced-SDV site such that messages, indicating SDV visits are likewise adjusted.

A site may be specified as a reduced-SDV site using any suitable criteria, as embodiments of the invention are not limited by the particular criteria used to specify a site as a reduced-SDV site. In some embodiments, authorized personnel at a clinical trial sponsor may be provided with a user interface that enables the user to specify the criteria for specifying a site as a reduced-SDV site. In some embodiments, sites may be associated with different amounts (e.g., percentages) of reduced SDV, and the appropriate amount of reduced SDV for a site may be determined based, at least in part, on a level of risk associated with the site. For example, low risk sites may be associated with a more reduced SDV, medium risk sites may be associated with a less reduced SDV, and high risk sites may be associated with no reduced SDV (i.e., all data may be required to be verified for high risk sites). Risk associated with a site may be determined in any suitable way, as discussed in more detail below. In some embodiments, the status of a site as a reduced-SDV site may be changed during a clinical trial based, at least in part, on one or more quality issues and/or data quality concerns reported by the trial monitor assigned to the site, or the status of the site may be changed for any other suitable reason.

A corresponding workload for a particular site may be determined based, at least in part, on whether the particular site is a reduced-SDV site. As discussed above, in some embodiments, each workload task may be associated with a particular amount of time. Accordingly, when a site is specified as a reduced-SDV site, the time associated with the workload task of source data verification may be reduced by an amount corresponding to the amount of reduced SDV for the site. For example, if the site is specified as an 50% reduced-SDV site, the corresponding workload for the workload task of verifying source data at the site may be reduced by 50%. Any suitable process may be used to determine workload based, at least in part, on reduced SDV, and the example described above is provided merely for illustrative purposes.

A determination of workload for a particular site may be performed at any suitable time intervals and/or in response to a user query, as embodiments of the invention are not limited in this respect. For example, in some embodiments, as new data is received by the information technology systems, the workload for a site may be updated in real time to provide a revised workload determination. Additionally, in some embodiments, a determination of workload for a particular site may be based, at least in part, on a projection of future workload for the site. A forecasted workload for a site may be based on factors including, but not limited to, expected or planned site or study subject recruitment rate, site or study withdrawal rate, study visit schedule, SDV schedule, historic patterns in site issues, and any other suitable workload factors. In some embodiments, forecasted workload for a site may be determined using one or more clinical trial forecasting tools configured to forecast one or more aspects of a clinical trial, wherein the one or more aspects include, but are not limited to, subject recruitment, regulatory compliance, and site monitoring. In some embodiments, forecasting of workload across clinical trials may be used by trial monitors to manage utilization of their monitoring resources.

As shown in FIG. 3, a site prioritization value for a site may also be based, at least in part, on one or more risk indicators 312 for a site. Any suitable risk indicators 312 may be used to determine a risk associated with a particular site in a clinical trial, as embodiments of the invention are not limited in this respect. Non-limiting examples of risk indicators 312 that may be used to determine a risk for a site in a clinical trial include a screening failure rate, an adverse event reporting rate, an absence of reported adverse events, a concomitant medication (i.e., medications taken concurrently with the investigational product) reporting amount, an amount of reported serious adverse events, an amount of protocol deviations, an amount and severity of site issues, and a data entry correction amount. Data associated with one or more of the risk indicators 312 may be received from an information technology system configured to process the data. In some embodiments, the data received from the information technology system may be further processed to determine one or more metrics that are used to determine a risk for a particular site. For example, data describing a number of patients screened and a number of patients enrolled may be received from an IVRS/IWRS system, and based on this data, a screening failure rate metric (e.g., 80%) may be determined for the site. Other data received from an information technology system may be used directly (i.e., without further processing) to determine a risk associated with a site. For example, a number of serious adverse events (SAEs) for a site may be received from a safety management or EDC system, and this number may be used directly in determining a risk associated with the site.

Figure 5:
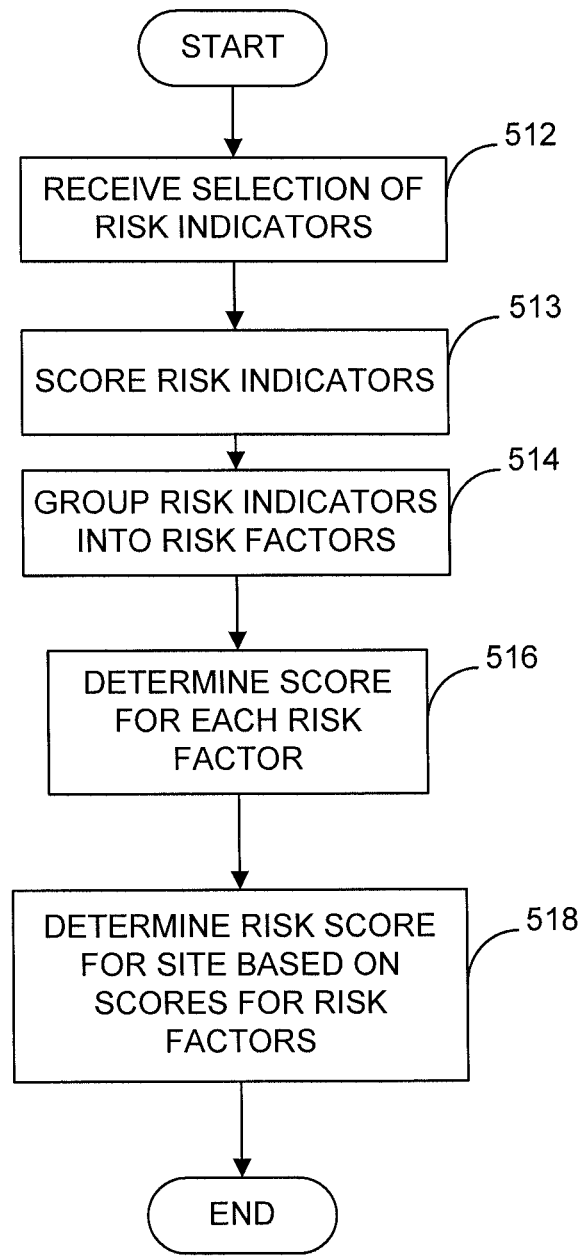
FIG. 5 is a flowchart of an illustrative process for determining a risk score for a site in a clinical trial in accordance with some embodiments of the invention.

Risk associated with a site may be determined in any suitable way, using any suitable algorithm, as embodiments of the invention are not limited in this respect. FIG. 5 shows an illustrative process for determining risk associated with a site in accordance with some embodiments of the invention. In act 512, a selection of one or more risk indicators is received. The one or more risk indicators may be selected in any suitable way. For example, a user interface may be provided to enable a user to specify the one or more risk indicators for a clinical trial and/or a clinical trial sponsor.

Alternatively, authorized personnel at a clinical trial sponsor may specify the one or more risk indicators in any other suitable way including, but not limited to, informing personnel at a contract research organization which risk indicators to include in a determination of risk, and in turn, a programmer at the contract research organization may specify the risk indicators for the clinical trial in any suitable way. The risk indicators may be expressed in any suitable way. For example, some risk indicators may be converted to numeric or categorical score values, as illustrated in act 513. Such score values may be computed by weighting values for risk indicators, as discussed in more detail below, or in any other suitable way.

After receiving a selection of the risk indicators, the process proceeds to act 514, where the selected risk indicators are grouped into one or more risk categories described herein as "risk factors." Non-limiting examples of risk factors include patient safety, protocol adherence, site issues, and data quality. Examples of risk indicators that may be included in the patient safety risk factor include, but are not limited to, screening failure rate, adverse event reporting rate, concomitant medication reporting, and reporting of a serious adverse event. It should be appreciated that any suitable number of risk indicators (including a single risk indicator) may be grouped into a risk factor, as embodiments of the invention are not limited in this respect. Additionally, although only four risk factors are discussed above, any suitable number of risk factors may be used in accordance with the techniques described herein. In some embodiments, risk indicators are not grouped into risk factors, but are considered individually in the determination of risk for a site in a clinical trial.

After grouping the risk indicators into risk factors, the process proceeds to act 516, where a score is determined for each of the risk factors. The score for a risk factor may be determined in any suitable way. In some embodiments, a score may be determined for each of the risk indicators associated with a risk factor, and the score for each risk factor may be determined based, at least in part, on the individual scores for each risk indicator. In other embodiments, the score for a risk factor may be determined based on a pattern or combination of values of risk indicators. A pattern associated with a significant risk may result in addition of a particular amount, proportional to the amount of that risk, to the score. The score for each risk indicator and/or risk factor may be determined in any suitable way using any suitable algorithm or computation, as embodiments of the invention are not limited in this respect.

After determining a score for each risk factor, the process proceeds to act 518, where a risk score for a site is determined based, at least in part, on the risk scores determined for each of the risk factors, or alternatively, the risk scores determined for the risk indicators in embodiments that do not group the risk indicators into risk factors. The risk score for a site may be determined in any suitable way, as embodiments of the invention are not limited in this respect. In some embodiments, the risk score for a site may be determined by adding the risk scores determined for each risk factor. In other embodiments, one or more of the risk scores determined for the risk factors may be weighted, such that different risk factors are emphasized (or de-emphasized) in the determination of the risk score for a site, as discussed in more detail below. It should be appreciated that the illustrative process of FIG. 5 does not limit embodiments of the invention, but is provided merely for illustrative purposes, and risk for a site in accordance with the techniques described herein may be determined in any suitable way.

As discussed briefly above, in some embodiments, the contribution of some risk indicators and/or risk factors in determining a risk for a site may depend on weights assigned to the risk indicators and/or risk factors. For example, some risk indicators, such as the number of reported SAEs or the number of reported protocol violations may provide a better indication that a site should be considered "high-risk" than other risk indicators such as a high screening failure rate or a low rate of reporting concomitant medications. Though, it is not necessary that weights be assigned to individual risk indicators or risk factors. In some embodiments, for example, weights may be assigned based on a pattern or combination of risk indicators or risk factors being present at a site. It should be appreciated that the above-provided example of weighting certain risk indicators and/or risk factors higher than others is provided merely for exemplary purposes and does not limit embodiments of the invention.

Weights for the risk indicators and/or risk factors may be specified in any suitable way. For example, in some embodiments, a user interface may be provided that enables a user to specify the weights for particular risk indicators and/or risk factors, and the weights may differ for each clinical trial and/or for each clinical trial sponsor. As discussed above, in some embodiments, a user associated with a clinical trial sponsor may be provided access to the user interface to specify the weights and/or risk indicators that are used to determine a site risk. In other embodiments, a programmer associated with a contract research organization may be provided with a user interface to specify the weights using one or more computer programs that interact with the data received from the information technology systems to determine risk associated with particular sites in a clinical trial.

Figure 6:
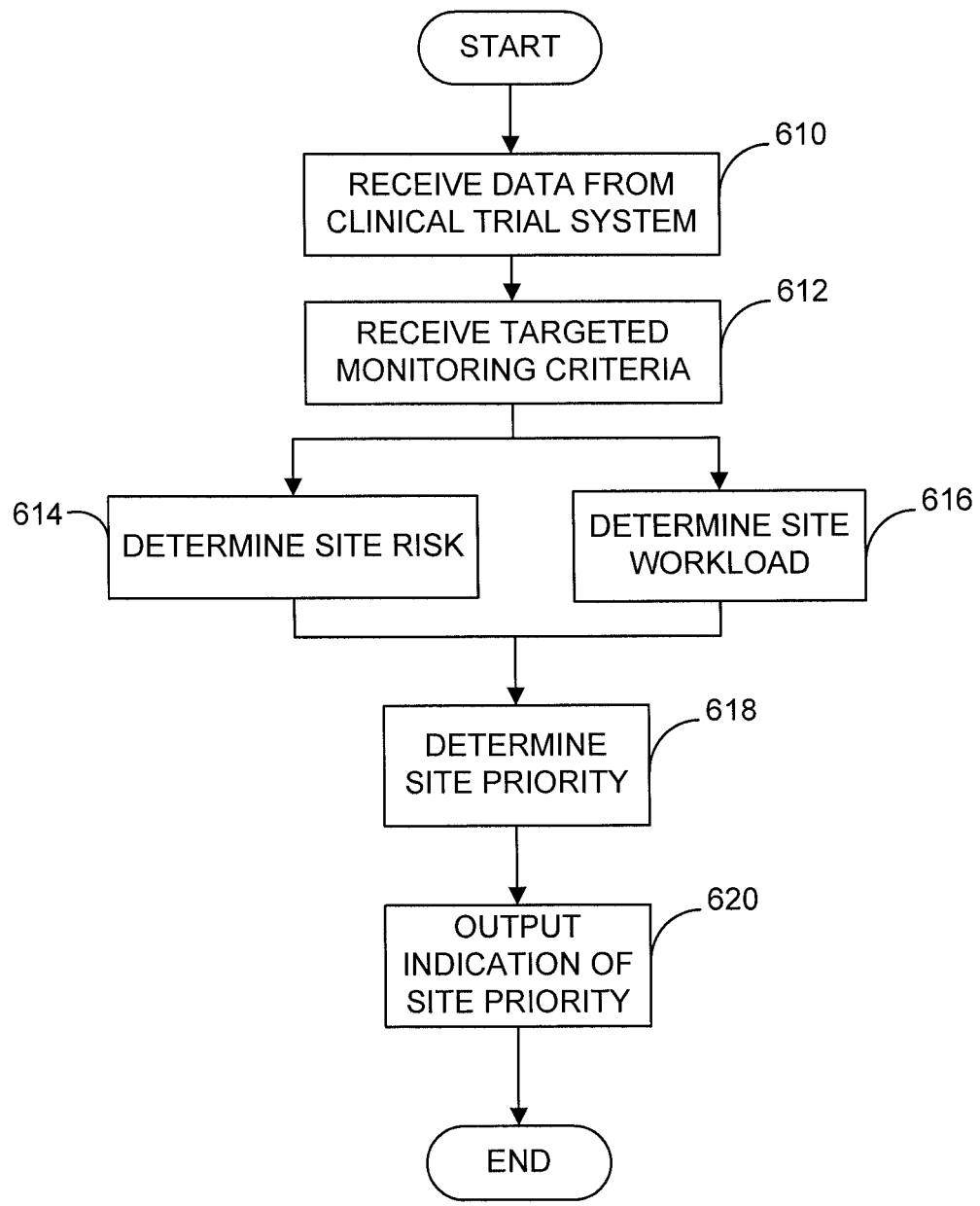
FIG. 6 is a flowchart of an illustrative process for determining a site prioritization in accordance with some embodiments of the invention.

FIG. 6 shows an illustrative process for determining a site prioritization for a site based, at least in part, on a site workload and a site risk, in accordance with the techniques described herein. In some embodiments, factors other than workload and risk may be considered in determining a site prioritization for a site, as discussed in more detail below. In act 610, data is received from at least one information technology system configured to process clinical trial data. The data may be received in any suitable way. In some embodiments, data may be retrieved from one or more information technology systems employed by a clinical research organization offering a trial management service, wherein each of the information technology systems is configured to facilitate one or more aspects of a clinical trial. The information technology systems may be stand-alone systems or at least some of the systems may be integrated using a platform that provides users with access to some or all of the systems via a common interface, as discussed above in connection with FIG. 2.

In one implementation, at least one processor may be programmed to receive as input, data from the one or more information technology systems and determine a site prioritization based on the input data using any suitable technique including, but not limited to, the techniques described above. As described in more detail below, the site prioritization may be determined based, at least in part, on one or more criteria specified by an administrator, a clinical trial sponsor, or any other authorized person. A determination of the site prioritization for a site may be initiated manually or automatically. For example, the site prioritization may be recalculated automatically in response to receiving new and/or revised data from one or more the information technology systems. Alternatively, the site prioritization may be determined in real-time, or on a scheduled basis (e.g., daily) or a determination of the site prioritization may be initiated in response to any suitable combination of data-driven and scheduling considerations.

In some embodiments, an initial site prioritization may be determined by the at least one processor, and a user may review this initial site prioritization as a suggestion for facilitating administration of monitoring activities in accordance with the techniques described herein. A user may then determine which monitoring resources to administer based, at least in part, on this suggestion and any suitable information the user may know. For example, if a user is aware that a site is planning on recruiting two patients next week, but they are not yet recorded in the EDC system, or if the user knows that a site investigator is unavailable certain days, this additional information may be used to facilitate monitoring resource decisions. In some embodiments, a user interface may be provided that enables a user to override the suggested initial site prioritization. In some embodiments, when a user overrides the suggested initial site prioritization, the user may be prompted to provide a reason for the override. The provided reason for the override may then be provided to the clinical trial sponsor or any other suitable entity upon request.

The particular manner in which the data is received as input to the at least one processor does not limit embodiments of the invention. In some embodiments, data may be retrieved (e.g., pulled) from the one or more information technology systems in response to a request from the at least one processor. Alternatively, the data may be sent (e.g., pushed) from the one or more information technology systems to the at least one processor for analysis without a request. Additionally, the data may be automatically retrieved from the multiple systems or the data may be provided to the at least one processor for analysis by at least one user.

After the data has been received from the one or more information technology systems, the process of FIG. 6 proceeds to act 612, where criteria are received, wherein the criteria inform a process of determining a site prioritization for a site by selecting input factors that should be used in determining the site prioritization. By enabling the received criteria to be specified for each clinical trial and/or sponsor, the techniques described herein may be configurable to conform to the requirements of each individual sponsor and/or protocol and flexible to be able to respond to future changes in governmental regulations or guidance regarding the conduct of monitoring for clinical trials. In particular, because there may not be a universally-accepted definition of risk associated with clinical trials, the configurability of embodiments of the invention provides a flexible framework for assessing risk and implementing techniques directed to reducing such risk in clinical trials.

After receiving the criteria and the data from the information technology system(s), the process proceeds to act 614, where a risk for the site is determined based, at least in part, on at least some of the received data and at least some of the received criteria. A site risk may be determined using any suitable technique including, but not limited to the techniques described above in connection with FIG. 5. The process also proceeds to act 616, where a workload for the site is determined based, at least in part, on at least some of the received data and at least some of the received criteria. A site workload may be determined using any suitable technique including, but not limited to, the techniques described above in connection with FIG. 4. Determining a site risk and a site workload are illustrated in FIG. 6 as being performed in parallel, though it should be appreciated that determining a site risk and a site workload may alternatively be performed sequentially, and in any order. Additionally, determining a site risk and a site workload may be performed by the same processor or processors or different processors, as embodiments of the invention are not limited in this respect.

After determining a site risk and a site workload, the process proceeds to act 618, where a site prioritization is determined based, at least in part, on the determined site risk and the site workload. The site prioritization may be determined in any suitable way, using any suitable weighting and/or algorithm. In some embodiments, the site prioritization may reflect a risk score for a site. However, the site prioritization may more generally be based on a risk status. That status may be based, at least in part, on factors such as workload and triggers.

After the site prioritization has been determined, the process proceeds to act 620, where an indication of the site prioritization is output. Outputting the site prioritization may be performed in any suitable manner including, but not limited to, displaying an output visualization of the site priority, storing the site priority using one or more data stores, sending the indication of the site prioritization to at least one electronic device using one or more networks, and interacting with a monitor scheduling system to propose an initial monitoring schedule or changes to an existing monitoring schedule for at least one trial monitor. Non-limiting examples of output visualizations that may be provided in accordance with some embodiments of the invention are discussed in more detail below. Moreover, information may be output instead of or in addition to a site prioritization. In some embodiments, a computing system outputting site prioritization information may host a user interface through which a user may request additional information about the prioritization assigned to a site. That information may be presented as one or more "drill down" interfaces through which a user may access information about risk factors, risk indicators, risk factor scores, weightings or other information used in computing a site prioritization or useful in understanding or applying the site prioritization. The displayed information alternatively or additionally may include historic trends of site risk. These trends may be presented in any suitable way, including multivariate graphics in which correlations with other parameters, such as workload, may be visualized.

In addition, the trends and/or correlations may be used to adjust site visit prioritizations (e.g., by proposing changes to a monitoring schedule) or other parameters associated with risk-based treatment of specific sites. As a specific example, when data shows a repeating pattern in a risk score over time, higher risk periods may be predicted and based on this prediction, it may be proposed to increase scheduled visits for the predicted higher risk periods. These predictions may be made for individual sites and/or individual studies. Though, the predictions may be pooled across sites and/or across studies.

As discussed above, a site prioritization determined in accordance with one or more of the techniques described herein may be based, at least in part, on factors other than risk and workload, as shown in FIG. 3. For example, a site prioritization may be based, at least in part, on one or more trigger factors 314. In some embodiments, the presence of one or more trigger factors may override a site prioritization assigned to a site based, at least in part, on workload and/or risk. Any suitable other trigger factors may be specified for consideration when determining a site prioritization in accordance with the techniques described herein. Non-limiting examples of trigger factors include a reported serious adverse event, a reported protocol deviation or violation, and an emergency code break. An emergency code is used in a blinded study to reveal which treatment a patient is receiving and may occur when a blinded code assigned to an investigational product is unsealed by investigational site staff in response, for example, to an adverse reaction to the investigational product by a patient, or for any other reason.

Each of the aforementioned trigger factors describes a situation where the site prioritization associated with a site may be increased to deal with an unforeseen and negative event occurring at a site. Trigger factors may also include other scenarios that reflect one or more positive events occurring at a site, which may decrease the site prioritization. For example, as described above, in some embodiments, one or more sites in a clinical trial may be specified as a reduced-SDV site. To be specified as a reduced-SDV site, a site may have to meet certain milestones regarding one or more criteria such as patient safety, data quality, and protocol adherence. In some embodiments, a trigger factor may include a determination that a site has met one or more milestones for being specified as a reduced-SDV site, and a site prioritization may be determined based, at least in part, on this trigger factor. Any other suitable trigger factors may additionally or alternatively be used, as embodiments of the invention are not limited in this respect.

As discussed above, in some embodiments, a user interface is provided with which an administrator may interact to select data and/or weights for determining risk, workload, and/or triggers for use in data-driven monitoring in accordance with the techniques described herein. For example, the user interface may enable metrics to be selected, algorithms to be selected and modified, and the selected metric(s) and algorithm(s) may be combined into one or more numeric risk, workload, and/or trigger values to facilitate monitor scheduling in a clinical trial. Any suitable metrics or algorithms may be used and embodiments of the invention are not limited by the particular metrics or algorithms employed.

As shown in FIG. 3, in some embodiments, a site prioritization value may be determined based, at least in part, on time information 316 associated with sites in a clinical trial. For example, time information 316 may specify an amount of time since the last site visit. Time information 316 may also indicate a threshold amount of time between monitoring visits as specified in a clinical trial protocol or specified in some other way. Time information associated with a site may be used in any suitable way to determine a site prioritization in accordance with the techniques described herein. For example, the sites that have not been visited within a particular amount of time (e.g., 8 weeks) may be given a higher priority than sites that have been visited more recently. Time information for a site may be used in combination with any of the one or more input factors described in FIG. 3 or any other suitable input factor to determine a site prioritization value.

As shown in FIG. 3, in some embodiments, a site prioritization may be based, at least in part, on a geographic location 318 of a site. For example, in some embodiments, one or more of the data-driven processes described herein may facilitate the assignment of monitoring resources to multiple sites in a clinical trial and/or across clinical trials by coordinating travel to the multiple sites located in a geographic region to reduce an amount of travel and associated costs. For example, it may be determined that site visits should be scheduled for sites in Boston on January 10, Los Angeles on January 15, New York on January 20, and San Diego on January 31. In some conventional monitoring systems, a trial monitor assigned to these four sites may be instructed to travel to each of the sites in the order listed above. However, visiting the sites in this order would require multiple trips across the U.S. in the span of one month. Some embodiments of the invention may determine an efficient schedule for monitoring visits by delaying or accelerating various site visit dates based on geographic location of the sites. For example, in the example provided above, it may be determined that the monitor should visit the Boston and New York sites between January 10-15 and the Los Angeles and San Diego sites between January 20-25, thereby reducing the number of cross-country trips required to complete all of the site visits. Geographic location information 318 may be used alone or in combination with any of the one or more input factors shown in FIG. 3, or any other suitable input factor for determining a site prioritization.

As shown in FIG. 3, in some embodiments, a site prioritization may be determined based, at least in part, on centralized monitoring information 320. Centralized monitoring information 320 may include any suitable information indicating whether at least some work at a site can be performed remotely from the site rather than being performed during a site visit. Examples of work that may be performed remotely include, but are not limited to, data quality monitoring, and investigation of some protocol deviations.

Some central management services for clinical trials (e.g., a CRO) may provide a centralized monitoring service that enables some monitoring services to be provided remotely over a network-based connection (e.g., the Internet) rather than requiring the monitor to physically visit the site. Some embodiments of the invention may be configured to determine which monitoring activities can be performed remotely to further reduce expenses associated with site visits. In response to determining which activities can be performed remotely, such activities may manually or automatically be assigned to a central monitor for completion. In some embodiments, central monitors may be provided access to a network-accessible integrated clinical trial system that enables the monitors to provide centralized monitoring services for a clinical trial. Alternatively, the central monitor may access one or more of the information technology systems using any suitable user interface to perform centralized monitoring services.

A determination that some work at a site may be performed remotely may be used to determine a site prioritization in any suitable way, as embodiments of the invention are not limited in this respect. For example, in response to determining that a site has work that may be performed remotely, a workload determination for the site may be adjusted based, at least in part, on the amount of work that may be remotely performed, such that the workload determined for the site is less than if the centralized monitoring information was not taken into account. By taking centralized monitoring information into account when determining a site prioritization, monitoring resources (e.g., monitoring site visits) may be able to be assigned more infrequently for sites that include tasks that can be performed remotely. A determination of which work can be performed remotely may be made in any suitable way. For example, a CRO may indicate to a clinical trial sponsor its remote monitoring capabilities and the clinical trial sponsor may select which tasks may be performed remotely and which require a site visit. It should be appreciated that the workload tasks selected for remote monitoring may be determined in any other suitable way.

In some embodiments, information associated with more than one clinical trial may be used to assign a site prioritization to a site in a clinical trial. For example, if multiple sites from different clinical trials serviced by a common trial monitor are located in a similar geographic region, some embodiments of the invention will facilitate the scheduling of monitoring resources across the multiple clinical trials. As the site prioritization values for particular sites may change based on a variety of input factors, as discussed herein, a proposed schedule of monitoring activities for a trial monitor may also be updated frequently based on up-to-date information provided in accordance with the techniques described herein. For example, a trial monitor may be scheduled to visit a site for a first clinical trial in New York at the end of April, and the same trial monitor may be scheduled to visit a site for a second clinical trial in Connecticut at the beginning of May. If a triggering event occurs that requires the trial monitor to schedule a site visit to the Connecticut site in early April, it may be proposed to reschedule the New York site visit to early April, such that both sites located in a similar geographic area may be visited on the same trip.

Alternatively or additionally, a computing system configured to determine risks and site prioritizations may perform other functions. Such a system, for example, may calculate monitoring manpower needed for a study or group of studies. As another example, the system may forecast future monitoring resource needs. This information may be presented in any suitable way to any suitable entity. For example, the information may be used to generate reports for clinical operations management.

Figure 7:
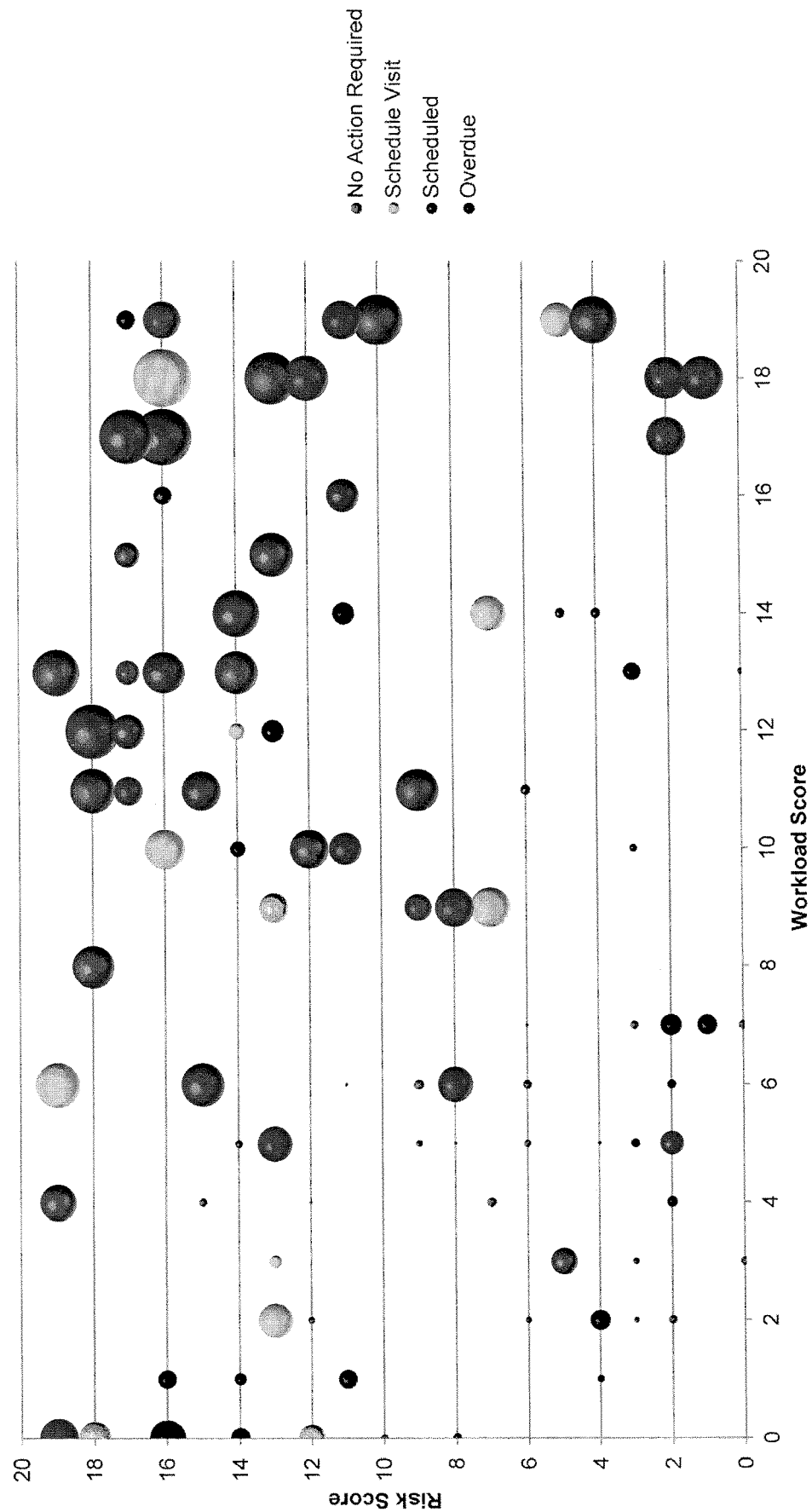
FIG. 7 is an example of an output visualization that may be generated in accordance with some embodiments of the invention.

In some embodiments, one or more output visualizations of an analysis of data received from the one or more information technology systems may be provided to facilitate assignment of monitoring resources. An output visualization may be provided in any suitable way including, but not limited to, using one or more graphs, charts, tables, or other illustrations that may help a user understand the analysis of the output to facilitate clinical trial monitoring. FIG. 7 shows an illustrative output visualization generated in accordance with some embodiments of the invention. In the output visualization of FIG. 7, each site in one or more clinical trials is represented by an indicator on a graph, wherein the size, shading, and location of each indicator on the output visualization is reflective of a site prioritization determined in accordance with one or more of the techniques described herein. In the illustrative graph of FIG. 7, a risk score and a workload score has been determined for each site, and the position of the corresponding indicator for the site reflects these scores. For example, sites associated with low risk and low workload scores have indicators positioned in the lower left portion of the graph, whereas sites associated with high risk and high workload scores have indicators positioned in the upper right portion of the graph.

A site prioritization may further be indicated by the shading of the indicator for particular sites. For example, although some sites may be associated with low risk and low workload scores, and thus have indicators positioned in the lower left of the graph of FIG. 7, such sites may nevertheless be require the assignment of monitoring resources based one or more of the other input factors discussed above (e.g., trigger factor, time-based factor). Sites that require the assignment of monitoring resources in the near future may be indicated using different (e.g., darker) shading than sites that do not require the assignment of monitoring resources in the near future. In some embodiments, different colors may be used to specify a site prioritization indication for a site. Additionally, other features of one or more indicators presented on an output visualization may also be used to indicate a site prioritization for a site. For example, as shown in FIG. 7, the size of an indicator may represent a site prioritization for a corresponding site, with larger indictors representing sites associated with a higher site prioritization value. Providing such information may inform a user of a site prioritization within a category such as "scheduled," to enable the user to make decisions about scheduling or rescheduling monitoring resources.

Any suitable output visualization may be used with embodiments of the invention, and the illustrative graph shown in FIG. 7 is merely one example of an output visualization that may be generated using the techniques described herein. For example, an output visualization may provide only information about site risk without providing information about site workload. Alternatively, an output visualization may provide information about site workload without providing information about site risk. Additionally, an output visualization may include information about any of the one or more other input factors used to determine a site prioritization value, as discussed above, and the information may be provided in any suitable way including, but not limited to, providing the information in a graph, a table, or a chart.

Figure 8:
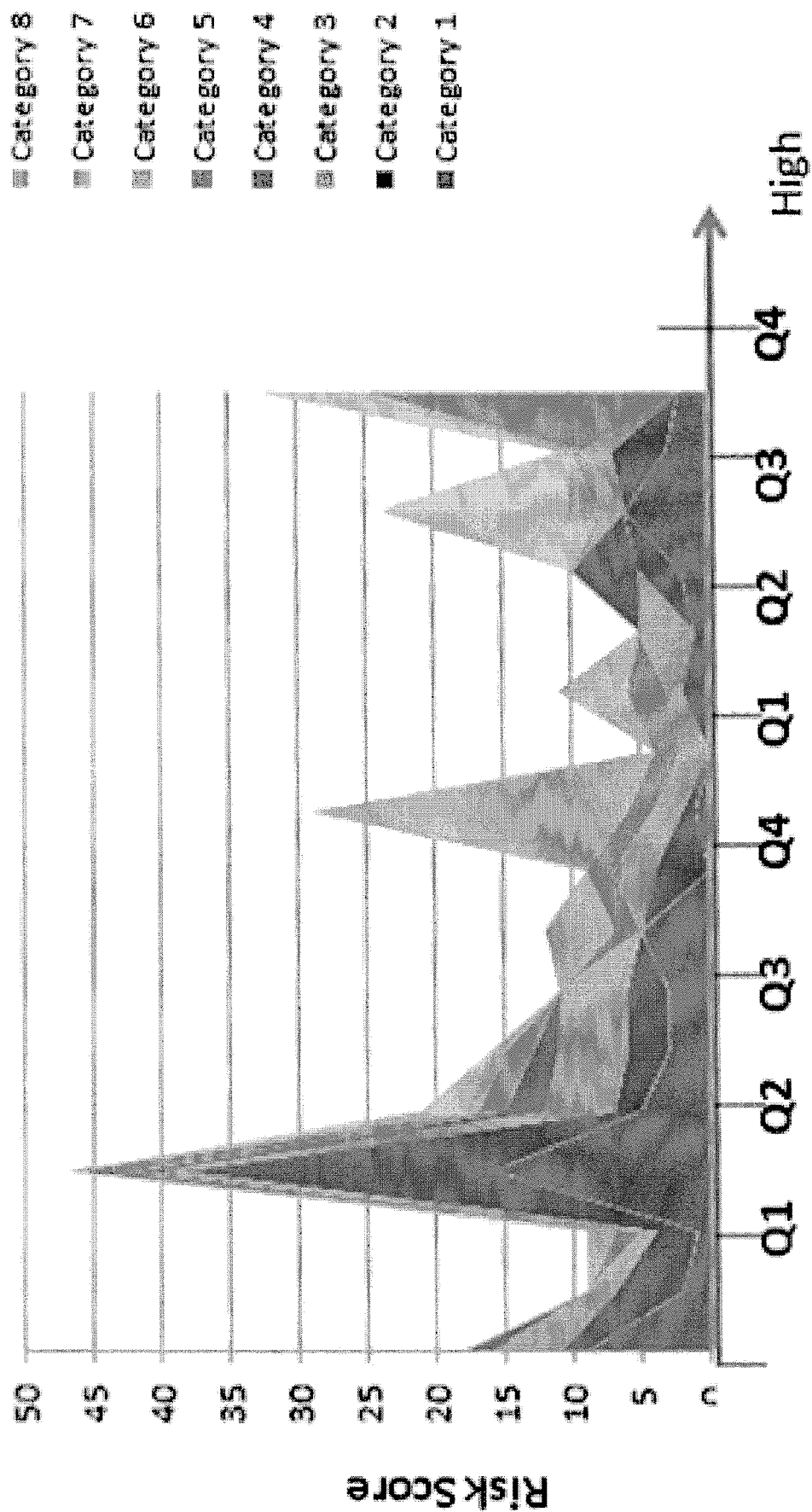
FIG. 8 is an example of another output visualization that may be generated in accordance with some embodiments of the invention.

FIG. 8 shows another illustrative output visualization that may be generated using one or more of the techniques described herein. In the output visualization of FIG. 8, changes in risk scores for a plurality of sites are shown as a function of time. As shown in this visualization, a time when risk for certain sites peaked and when an action was taken that resulted in the lowering of risk for the particular site may be determined. Such information may be useful for demonstrating to a regulatory agency or sponsor that oversight of site risk was being performed during the study and correct actions were performed to manage the risks at various sites in the clinical trial. The information included in an output visualization may be used for any other reason, as providing information to a regulatory agency or sponsor is merely one use for such information.

In some embodiments, an indication of a site prioritization may be output in association with monitor scheduling information by generating a monitor scheduling report based, at least in part, on site prioritization information for at least one site determined in accordance with the techniques described herein. The monitor scheduling report may generated in any suitable way. For example, in some embodiments, a monitor scheduling system may be accessed to determine a scheduled monitoring visit for at least one site and/or at least one trial monitor. A site prioritization value determined based, at least in part, on the techniques described herein, may be used to provide suggestions for updating a scheduled monitoring visit. For example, it may be determined whether a particular site is associated with a site prioritization value below a particular threshold. If it is determined that the site prioritization value is below the threshold, a suggestion to reschedule at least one scheduled monitoring visit stored by the monitor scheduling system may be provided to enable the trial monitor to assess whether to reschedule the monitoring visit.

In some embodiments, a determination of whether to provide a suggestions to reschedule a scheduled monitoring visit based, at least in part, on a site prioritization value may also be based on other factors including, but not limited to, a geographical location of a plurality of sites for which monitoring visits should be scheduled. Any suitable input factors including, but not limited to those discussed above, for determining a site prioritization value may be used to determine whether to provide a suggestion to reschedule a scheduled monitoring visit, as embodiments of the invention are not limited in this respect.

In some embodiments, a user interface may be provided to enable a trial monitor to interact with one or more of the output visualizations, tabular data, and site prioritizations to decide how to assign monitoring resources for the sites in the clinical trial. For example, assigning monitoring resources may include, but is not limited to, determining which sites to visit, which sites to contact remotely, and which sites do not require contact at a particular point in time. In such embodiments, one or more tools may be provided to enable a trial monitor to schedule their monitoring work, accounting for the time each visit or contact is estimated to take, including time for travel, if applicable. These tools may be provided as part of a stand-alone system or may be integrated with a monitoring visit management and reporting system. Additionally, a user (e.g., trial monitor or operations manager) may be able to interact with the user interface to assign tasks (e.g., visits or contacts) to other trial monitors as required by the clinical trial.

In some embodiments, a user may interact with the user interface to perform at least one task, such as specifying one or more reasons for taking certain actions (e.g., not performing/postponing a site visit, replace a site visit by centralized monitoring activities) and this information may be recorded, tracked, and provided to regulators or management, as discussed above to explain how the monitoring approach was adhered to and to illustrate that contractual, regulatory, and good clinical practices (GCP) requirements have been fulfilled. Such information may be provided to regulators or management in any suitable way including, but not limited to, generating a report that includes at least a portion of the information. For example, in some embodiments, a report may be generated that includes an indication of one or more reasons for taking a certain action (e.g., not performing a site visit), and the report may be provided to a regulator or management.

The user interface may be configured in any suitable way. For example, in some embodiments, the user interface may display a task panel showing scheduled activities for each trial monitor and/or team of trial monitors. An operations manager or other authorized person may interact with the user interface to make decisions about assigning monitoring resources within a clinical trial and/or across multiple clinical trials. In some embodiments, feedback from one or more monitoring systems may provide a data-driven monitoring system with information when monitoring activities (e.g., scheduled site visits) have been completed so they can be removed from the task panel and to reset site prioritization calculations.

In some embodiments, the user interface may be configured to enable a user to visualize an assigned site prioritization for one or more sites in a clinical trial, wherein the site prioritization is an initial site prioritization, as discussed above. The user may provide user input that revises the initial site prioritization, and the revised site prioritization may be displayed on the user interface. A non-limiting example of user input that may result in a revised site prioritization is user input in a CTMS that changes the monitoring status of a site in a clinical trial. For example, a site status associated with a site may initially be specified as "visit required." Once a site visit has been confirmed as having been planned, the site status associated with the site may change in the CTMS from "visit required" to "visit planned or scheduled," with the planned site visit to be confirmed by a trial monitor or other suitable clinical trial team member. After a site visit has been confirmed as completed in the CTMS, the site status associated with the site may be changed to "visit completed." In response to receiving user input corresponding to the changes in site status, a revised site prioritization may be determined based on the received user input, and an indication of the revised site prioritization may be stored in a data store associated with at least one processor configured to perform one or more of the techniques described herein.

In some embodiments, the user interface may present monitoring priorities, workload, and/or site risk for sites within a clinical trial and/or consolidated across clinical trials. In some embodiments, not all clinical trials may be weighted equally. For example, higher weights may be specified for certain clinical trials when consolidating data based on aspects of the trial that pertain to the relative level of risk or attention it should receive.

As discussed above, in some embodiments, one or more data-driven processes to facilitate data-driven monitoring may be implemented using an integrated clinical trial platform that incorporates a plurality of modules for planning, managing, and conducting various aspects of a clinical trial. One or more users (e.g., centralized monitor, operations manager, clinical trial sponsors, administrators, etc.) may interact with a user interface provided by the integrated clinical trial platform to retrieve, modify, and or view the one or more output visualizations created in accordance with some embodiments of the invention. It should be appreciated however, that not all embodiments are limited to use with an integrated clinical trial platform, as any suitable connection between information technology systems configured to process clinical trial data may be used in accordance with embodiments of the invention.

Site prioritization information determined in accordance with one or more of the techniques described herein may be output by providing information to one or more of the information technology systems configured to process clinical trial data. For example, in response to determining that a site has met criteria for being specified as a reduced-SDV site, information may be manually or automatically provided to an electronic data capture (EDC) system to associate the site with a reduced-SDV configuration. By providing such information automatically between network-connected information technology systems, the process of clinical trial monitoring may be improved without requiring a user to input the information into each system individually.

The foregoing techniques for facilitating clinical trial monitoring may be implemented in any suitable computing device or devices. An illustrative implementation of a computer system 100 on which some or all of the techniques and/or user interactions described herein may be implemented is shown in FIG. 1. The computer system 100 may include one or more processors 110 and one or more computer-readable non-transitory storage media (e.g., memory 120 and one or more non-volatile storage media 130). The processor(s) 110 may control writing data to and reading data from the memory 120 and the non-volatile storage device 130 in any suitable manner, as the aspects of the present invention described herein are not limited in this respect.

To perform any of the functionality described herein, the processor(s) 110 may execute one or more instructions, such as program modules, stored in one or more computer-readable storage media (e.g., the memory 120), which may serve as non-transitory computer-readable storage media storing instructions for execution by the processor 110. Generally, program modules include routines, programs, objects, components, data structures, etc. that perform particular tasks or implement particular abstract data types. Embodiments may also be implemented in distributed computing environments where tasks are performed by remote processing devices that are linked through a communications network. In a distributed computing environment, program modules may be located in both local and remote computer storage media including memory storage devices.

Computer 100 may be arranged to be in communication with one or more databases that store information related to one or more clinical trials. For example, each of the information technology systems described above (e.g., EDC, RTSM, CTMS) may include one or more associated databases that store information specific to each system. Alternatively, one or more databases may store data that is shared between different systems and the particular implementation of how data is stored in a computer system does not limit embodiments of the invention. Computer 100 may be configured to access some or all of the data from such databases using any suitable network connection, as described in more detail below.

The information technology systems may interact and/or share data in any suitable manner. For example, in some embodiments, computer 100 may be connected to particular information technology systems (e.g., CTMS, Monitoring Visit report management systems) such that site visits proposed by the data-driven monitoring system are referenced and reported in the CTMS, and an indication that visits have been completed may be returned to computer 100 and such information may be stored by data store 130 associated with the computer 100. Additionally, a data-driven monitoring system implemented in accordance with the techniques described herein may be configured to interact with an EDC system to dictate changes to the source data verification (SDV) strategy for each site based, at least in part, on risk and data quality measures. Updates to the EDC system in this manner may subsequently inform associated workload calculations for particular sites, as described above.

Computer 100 may operate in a networked environment using logical connections to one or more remote computers. The one or more remote computers may include a personal computer, a server, a router, a network PC, a peer device or other common network node, and typically include many or all of the elements described above relative to the computer 100. Logical connections between computer 100 and the one or more remote computers may include, but are not limited to, a local area network (LAN) and a wide area network (WAN), but may also include other networks. Such networks may be based on any suitable technology and may operate according to any suitable protocol and may include wireless networks, wired networks or fiber optic networks. Such networking environments are commonplace in offices, enterprise-wide computer networks, intranets and the Internet.

When used in a LAN networking environment, the computer 100 may be connected to the LAN through a network interface or adapter. When used in a WAN networking environment, the computer 100 typically includes a modem or other means for establishing communications over the WAN, such as the Internet. In a networked environment, program modules, or portions thereof, may be stored in the remote memory storage device.

Various inputs described herein for facilitating data-driven monitoring may be received by computer 100 via a network (e.g., a LAN, a WAN, or some other network) from one or more remote computers that stores data associated with the inputs. One or more of the remote computers may perform analysis on remotely-stored data prior to sending analysis results as the input data to computer 100. Alternatively, the remotely stored data may be sent to computer 100 as it was stored remotely without any remote analysis. Additionally, inputs may be received directly by a user of computer 100 using any of a number of input interfaces that may be incorporated as components of computer 100, examples of which are provided below.

Various outputs described herein, including output visualizations, may be provided on an output device (e.g., a display) connected directly to computer 100 or the output(s) may be provided to a remotely-located output device connected to computer 100 via one or more wired or wireless networks, as embodiments of the invention are not limited in this respect. In some embodiments, output visualizations are provided via a web-based portal accessible to users of a clinical trial system in response to providing authentication information (e.g., username, password).

It should be appreciated that although computer 100 is illustrated in FIG. 1 as being a single device, in some embodiments, computer 100 may comprise a plurality of devices communicatively coupled to perform some or all of the functionality described herein, and computer 100 is only one illustrative implementation of a computer that may be used in accordance with embodiments of the invention.

Having thus described several aspects of at least one embodiment of this invention, it is to be appreciated that various alterations, modifications, and improvements will readily occur to those skilled in the art.

Various aspects of the present invention may be used alone, in combination, or in a variety of arrangements not specifically discussed in the embodiments described in the foregoing and are therefore not limited in their application to the details and arrangement of components set forth in the foregoing description or illustrated in the drawings. For example, aspects described in one embodiment may be combined in any manner with aspects described in other embodiments.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a tablet computer, a smart phone or any other suitable portable or fixed electronic device.

Also, a computer may have one or more input and output devices. These devices can be used, among other things, to present a user interface, as described above. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a non-transitory tangible computer readable storage medium (or multiple computer readable storage media (e.g., a computer memory, a USB drive, a flash memory, a compact disk, a tape, etc.) encoded with a computer program (i.e., a plurality of instructions), which, when executed on a processor, performs one or more of the functions of the embodiments of the present invention. The computer-readable storage medium can be transportable such that the program stored thereon can be loaded onto any computer resource to implement the aspects of the present invention discussed herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the present invention. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Also, the techniques described herein may be embodied as a method, of which an example has been provided. The acts performed as part of the method may be ordered in any suitable way. Accordingly, embodiments may be constructed in which acts are performed in an order different than described, which may include performing some acts simultaneously, even though described as sequential acts in illustrative embodiments.

What is claimed is:

1. A method of facilitating monitoring in at least one clinical trial, the method comprising:
   receiving, from at least one information technology system configured to process clinical trial data in connection with an on-going clinical trial of the at least one clinical trial, data from a plurality of sites for the on-going clinical trial associated with the at least one information technology system, wherein the clinical trial data is communicated via a communication network from the plurality of sites to the at least one information technology system;
   deriving risk information from the received data, wherein deriving risk information comprises:
      determining risk scores for individual sites of the plurality of sites based, at least in part, on the data received from the at least one information technology system,
      the data received from the at least one information technology system comprising a plurality of risk indicators;
   computing, from the received data, workload information for the plurality of sites, wherein the received data comprises information on tasks associated with individual sites of the plurality of sites to be performed based on clinical trial data stored during the on-going clinical trial in the at least one information technology system, and wherein computing the workload information comprises:
      determining tasks for individual sites of the plurality of sites based, at least in part, on the data received from the at least one information technology system,
      assigning time components to individual tasks, and
      determining total workload times for individual tasks for the sites based, at least in part, on the assigned time components and the data received from at least one information technology system associated with corresponding tasks;
   computing, using at least one processor, a site prioritization value for each of the plurality of sites for the on-going clinical trial based, at least in part, on the derived risk information and the workload information, wherein the site prioritization values indicate an urgency with which monitoring resources should be assigned to respective sites, wherein computing the site prioritization value comprises assigning the site prioritization value for each of the plurality of sites based, at least in part, on a corresponding risk score determined for the site;
   adjusting, dynamically during the on-going clinical trial, the site prioritization values for the plurality of sites, based at least in part on the respective risk scores and the workload information determined from portions of the received data entered in the at least one information technology system during the on-going clinical trial, wherein the site prioritization values for the plurality of sites change dynamically during the on-going clinical trial based at least in part on changes of the risk information and changes of the workload information; and
   outputting the site prioritization values to a monitor scheduling system associated with at least one trial monitor of the on-going clinical trial, wherein the monitor scheduling system is configured to generate a schedule of monitoring actions based on the site prioritization values, such that the schedule is dynamically adjusted based at least in part on the data entered in the at least one information technology system during the on-going clinical trial and workload information, wherein the schedule of monitoring actions is different than an initial schedule of monitoring actions for the on-going clinical trial.

2. The method of claim 1, further comprising:
   receiving criteria for a clinical trial of the at least one clinical trial and/or a clinical trial sponsor, wherein the criteria includes at least one task and/or at least one risk indicator; and
   wherein computing the site prioritization value is based, at least in part, on the criteria.

3. The method of claim 2, wherein the criteria includes at least one workload task and at least one risk indicator, and wherein computing the site prioritization based, at least in part, on the criteria comprises:
   determining a workload score for a site based, at least in part, on the data received from at least one information technology system associated with the at least one workload task;

determining the risk score for the site based, at least in part, on the data received from at least one information technology system associated with the at least one risk indicator; and assigning the site prioritization value for a site based, at least in part, on the workload score for the site and the risk score for the site.

4. The method of claim 2, wherein the criteria further includes at least one trigger factor selected from the group consisting of a serious adverse event, a reported protocol deviation, an emergency code break, and a determination that a site of the plurality of sites has met a milestone for being specified as a reduced source data verification site; and wherein computing the site prioritization value is further based, at least in part, on the at least one trigger factor.

5. The method of claim 2, wherein the criteria further includes at least one trigger factor specified by user input; and wherein computing the site prioritization is further based, at least in part, on the at least one trigger factor.

6. The method of claim 1, wherein computing the workload information for the plurality of sites comprises:

determining workloads for individual sites based, at least in part, on the workload for the sites.

7. The method of claim 1, further comprising:

outputting, via a user interface, an indication of the workload information determined for one or more of the plurality of sites.

8. The method of claim 2, wherein the criteria further include an amount of time that has passed since the last site visit.

9. The method of claim 1, further comprising:

outputting, via a user interface, an indication of the risk information determined for one or more of the plurality of sites.

10. The method of claim 1, wherein determining risk scores for individual sites of the plurality of sites comprises:

determining, based at least in part on the received data, a value of each of at least a portion of the plurality of risk indicators for each site of the plurality of sites;

grouping the plurality of risk indicators into individual risk factors;

determining a score for individual risk factors based on the values of groups of the plurality of risk indicators corresponding to individual risk factors; and determining the risk score for each site of the plurality of sites based, at least in part, on the scores for individual risk factors associated with the site.

11. The method of claim 10, wherein the risk factors include a risk factor selected from the group consisting of patient safety, protocol adherence, site issues, and data quality.

12. The method of claim 1, wherein the plurality of risk indicators include a risk indicator selected from the group consisting of a screening failure rate, an adverse event reporting rate, an absence of reported adverse events, a concomitant medication reporting amount, a number of reported serious adverse events, a number of protocol deviations, a number of site issues, and a data entry correction amount.

13. The method of claim 1, wherein:

the workload information further includes indications of whether the tasks can be performed remotely from a site, and a task that is indicated as capable of being performed remotely is selected from a group of tasks comprising data quality monitoring and investigation of protocol deviations.

14. The method of claim 13, wherein, when a workload information of a site indicates that the site has at least one task that can be performed remotely, the site prioritization value determined for a site is less than that if the workload information of the site indicates that the site has no task that can be formed remotely.

15. The method of claim 13, wherein, when a task at a site is indicated as capable of being performed remotely, monitoring is performed at least in part over a network connection from a centralized location to the site.

16. The method of claim 1, wherein computing the site prioritization value to each of the plurality of sites for the on-going clinical trial is further based, at least in part, on a geographic location of a site.

17. The method of claim 1, further comprising:

sending a request to the at least one information technology system to provide the data; and wherein the receiving data from at least one information technology system comprises receiving the data from the at least one information technology system in response to sending the request.

18. The method of claim 1, wherein the at least one information technology system includes at least one system selected from a group consisting of an electronic data capture (EDC) system, a clinical trial management system (CTMS), a randomization and trial supply management (RTSM) system, a medical imaging system, an ECG management system, an electronic patient reported outcomes system, a drug safety system, and a central laboratory data system.

19. The method of claim 1, wherein computing the site prioritization value to each of a plurality of sites for the on-going clinical trial comprises assigning a risk category to each of a plurality of sites for each of at least two clinical trials associated with the at least one information technology system.

20. The method of claim 1, wherein outputting the site prioritization values comprises displaying, on a user interface, an output visualization with which a user may interact to perform at least one task.

21. The method of claim 20, wherein performing the at least one task comprises assigning a task to a person such as a monitor and/or specifying at least one reason for taking a certain action.

22. The method of claim 21, wherein specifying at least one reason for taking a certain action comprises interacting with the user interface to input at least one reason describing why a monitoring visit was not scheduled.

23. The method of claim 21, further comprising:

generating a report, wherein the report includes an indication of the at least one reason for taking the certain action.

24. The method of claim 1, wherein the site prioritization value comprises an initial site prioritization value, and wherein the method further comprises:

receiving, via the user interface, user input that revises the initial site prioritization value; and storing a revised site prioritization value determined based, at least in part, on the received user input.

25. The method of claim 1, further comprising:
receiving information from a monitoring visit system configured to process clinical trial data, wherein the information indicates that at least one monitoring visit has been completed; and
updating the site prioritization value for at least one site based, at least in part, on the received information from the monitoring visit system.

26. A non-transitory computer-readable medium encoded with a plurality of computer-executable instructions that, when executed by at least one processor, perform a method comprising:
configuring a site monitoring system based on received information specifying criteria associated with a clinical trial protocol, wherein the site monitoring system is configurable such that risk scores are based on the criteria associated with the clinical trial protocol;
during the course of the clinical trial:
receiving data associated with a plurality of risk indicators from at least one information technology system configured to process clinical trial data for a plurality of sites of at least one clinical trial;
determining, based at least in part on the received data, a value of each of the plurality of risk indicators for each site of the plurality of sites, wherein the determined values of the plurality of risk indicators include values of at least one risk indicator selected from the group consisting of an absence of reported adverse events, a concomitant medication reporting amount, a number of site issues, and a data entry correction amount;
for each site of the plurality of sites, grouping the plurality of risk indicators into individual risk factors, and determining scores for individual risk factors based on the values of groups of the plurality of risk indicators corresponding to individual risk factors;
computing a risk score for each site of the plurality of sites based on the scores for individual risk factors associated with the site;
computing a site prioritization value for each of the plurality of sites based, at least in part, on the risk score for each site of the plurality of sites;
adjusting, dynamically during the at least one clinical trial, the site prioritization value for each of the plurality of sites, based at least in part on changes of a corresponding risk score that is computed based on the scores for individual risk factors associated with the site; and
outputting, over at least one network to at least one electronic device, an indication of a timing and/or frequency and/or type of monitoring activities based on the site prioritization values such that the site prioritization values for the plurality of sites change dynamically during the at least one clinical trial based at least in part on changes of risk information and changes of workload information computed from the received data.

27. The method of claim 26, wherein determining the value for each of the plurality of risk indicators are based on weights assigned to each of the plurality of risk indicators.

28. The method of claim 26, wherein computing the risk score for each site of the plurality of sites comprises computing the risk score for each site of the plurality of sites based on weights assigned to each of the risk factors.

29. The method of claim 26, wherein the plurality of risk indicators are specified by user input for the at least one clinical trial and/or clinical trial sponsor.

30. A computer system comprising:
an input interface configured to receive data over a network from at least one information technology system configured to process clinical trial data conducted in accordance with a protocol, wherein the data includes data collected during an on-going clinical trial at a plurality of sites associated with the at least one information technology system;
at least one processor programmed to:
derive risk information based on criteria associated with the protocol from the received data associated with each site of the plurality of sites, wherein deriving risk information comprises determining a risk score for each site of the plurality of sites based, at least in part, on the data received from the at least one information technology system;
derive workload information from the received data associated with each site of the plurality of sites, wherein the workload information includes an indication of whether work can be performed remotely from at least one site of the plurality of sites;
compute a site prioritization value for each of the plurality of sites based, at least in part, on the risk information and the workload information, wherein computing the site prioritization value comprises assigning the site prioritization value for each of the plurality of sites based, at least in part, on a corresponding risk score determined for the site; and
adjust, dynamically during the at least one clinical trial, the site prioritization value for each of the plurality of sites, based at least in part on changes of a corresponding risk score and changes of the workload information derived from the received data; and
an output device configured to output an indication of a timing and/or frequency and/or type of monitoring activities based on the site prioritization values, wherein the site prioritization values for the plurality of sites change dynamically during the on-going clinical trial based at least in part on changes of the risk information and changes of the workload information.

31. The method of claim 1, wherein:
computing the site prioritization value to each of the plurality of sites comprises selecting a level of risk associated with a site of the plurality of sites, and
outputting a schedule of monitoring actions comprises selecting a type of monitoring action for the site of the plurality of sites based on the level of risk.

32. The method of claim 1, wherein:
outputting a schedule of monitoring actions includes assigning a first type of monitoring action, and assigning a second type of monitoring action in response to an outcome of the first type of monitoring action being performed.

33. The method of claim 1, wherein:
the method comprises identifying a first group of the plurality sites as having a lower level of risk than a second group of the plurality of sites, and
outputting a schedule of monitoring actions comprises scheduling monitoring actions for the first group of the plurality of sites at a lower frequency of occurrence than the second group of the plurality of sites.

34. The computer system of claim 30, wherein:
the at least one processor is further configured to detect patterns of the derived risk information over time; and computing the site prioritization value is based on predicting risk from the detected patterns.

35. A method of facilitating monitoring in an on-going clinical trial conducted in accordance with a protocol, the method comprising, using at least one processor to:
   receive, during the on-going clinical trial, from at least one information technology system configured to process clinical trial data, data corresponding to a plurality of sites for the on-going clinical trial associated with the at least one information technology system;
   compute risk information for each of the plurality of sites based on the received data and criteria comprising at least two of an amount of work at a site, a risk assessment of a site, a geographic location of a site, an amount of time that has passed since the last site visit, or triggering factors, wherein the criteria are configurable;
   compute a site prioritization value for each of the plurality of sites for the on-going clinical trial, wherein the assigning a site prioritization value is based, at least in part, on the computed risk information associated with individual sites of the plurality of sites, wherein the site prioritization value is a category of a plurality of predetermined categories indicating urgency with which monitoring resources should be assigned to a site, wherein computing the site prioritization value comprises assigning the site prioritization value for each of the plurality of sites based, at least in part, on a corresponding risk score determined for the site;
   adjust, dynamically during the on-going clinical trial, the site prioritization values for the plurality of sites, based at least in part on portions of the received data entered in the at least one information technology system during the on-going clinical trial, wherein the site prioritization values for the plurality of sites change dynamically during the on-going clinical trial based at least in part on changes of respective risk scores and changes of workload information computed from the received data; and
   output, to a user interface associated with at least one trial monitor of the on-going clinical trial, a schedule of monitoring actions based on the site prioritization values, such that the schedule is dynamically adjusted based at least in part on the data entered in the at least one information technology system during the on-going clinical trial, wherein the schedule of monitoring actions is different than an initial schedule of monitoring actions for the on-going clinical trial and includes a type of monitoring action selected for a site of the plurality of sites according to the prioritization value associated with the site.

36. A method of facilitating monitoring in at least one clinical trial, the method comprising:
   receiving, from at least one information technology system configured to process clinical trial data in connection with an on-going clinical trial of the at least one clinical trial, data from a plurality of sites for the on-going clinical trial associated with the at least one information technology system, wherein the clinical trial data is communicated via a communication network from the plurality of sites to the at least one information technology system;
   deriving risk information from the received data;
   computing, from the received data, workload information for the plurality of sites, wherein the received data comprises information on tasks associated with individual sites of the plurality of sites to be performed based on clinical trial data stored during the on-going clinical trial in the at least one information technology system, and wherein the workload information is computed from time components assigned to the tasks;
   computing, using at least one processor, a site prioritization value for each of the plurality of sites for the on-going clinical trial based, at least in part, on the derived risk information and the workload information, wherein the site prioritization values indicate an urgency with which monitoring resources should be assigned to respective sites, wherein computing the site prioritization value comprises assigning the site prioritization value for each of the plurality of sites based, at least in part, on a corresponding risk score determined for the site;
   adjusting, dynamically during the on-going clinical trial, the site prioritization values for the plurality of sites, based at least in part on respective risk scores and the workload information determined from portions of the received data entered in the at least one information technology system during the on-going clinical trial, wherein the site prioritization values for the plurality of sites change dynamically during the on-going clinical trial based at least in part on changes of the risk information and changes of the workload information; and
   outputting the site prioritization values to a monitor scheduling system associated with at least one trial monitor of the on-going clinical trial, wherein the monitor scheduling system is configured to generate a schedule of monitoring actions based on the site prioritization values, such that the schedule is dynamically adjusted based at least in part on the data entered in the at least one information technology system during the on-going clinical trial and workload information, wherein the schedule of monitoring actions is different than an initial schedule of monitoring actions for the on-going clinical trial,
   wherein the workload information includes a total workload and wherein computing the workload information for the plurality of sites comprises:
      determining a workload for each of the plurality of sites based, at least in part, on the data received from at least one information technology system;
      assigning a time component to each task of the tasks;
      determining a total workload time for each task of the tasks for the site, wherein the determining a total workload time is based, at least in part, on the assigned time components and the data received from at least one information technology system associated with a corresponding task of the at least one workload task for the site; and
      determining the total workload for the site is based, at least in part, on the total workload time for each task of the at least one workload task for the site,
   wherein the received data include data associated with a plurality of risk indicators, and wherein deriving risk information comprises:
      determining a risk score for each of the plurality of sites based, at least in part, on the data received from at least one information technology system associated with the plurality of risk indicators; and
      placing each of the plurality of sites into one of a predetermined number of categories based on a corresponding risk score,
   wherein computing the site prioritization based, at least in part, on the criteria comprises assigning the site prioritization for each of the plurality of sites based, at least in part, on a corresponding risk score determined for the site.

\* \* \* \* \*